(12) United States Patent
Degen

(10) Patent No.: US 8,702,745 B2
(45) Date of Patent: Apr. 22, 2014

(54) BALLOON OF A BALLOON CATHETER

(76) Inventor: Nicolas Degen, Beringen (CH)

(*) Notice: Subject to any disclaimer, the term of this patent is extended or adjusted under 35 U.S.C. 154(b) by 180 days.

(21) Appl. No.: 13/055,341

(22) PCT Filed: May 18, 2009

(86) PCT No.: PCT/EP2009/003528
§ 371 (c)(1),
(2), (4) Date: Aug. 18, 2011

(87) PCT Pub. No.: WO2010/009785
PCT Pub. Date: Jan. 28, 2010

(65) Prior Publication Data
US 2011/0295201 A1    Dec. 1, 2011

(30) Foreign Application Priority Data

Jul. 23, 2008  (EP) .................................. 08013291

(51) Int. Cl.
*A61M 29/00*  (2006.01)
*A61M 31/00*  (2006.01)
*A61M 37/00*  (2006.01)

(52) U.S. Cl.
USPC ..................................... 606/194; 604/103.07

(58) Field of Classification Search
USPC ......... 604/103.06–103.08, 509; 606/191–200
See application file for complete search history.

(56) References Cited

U.S. PATENT DOCUMENTS

| 5,759,172 | A   | * | 6/1998  | Weber et al.      | 604/103.07 |
| 6,296,655 | B1  | * | 10/2001 | Gaudoin et al.    | 606/194    |
| 2003/0163157 | A1 |   | 8/2003  | McMorrow et al.   |            |
| 2005/0177130 | A1 |   | 8/2005  | Konstantino et al.|            |
| 2008/0097300 | A1 | * | 4/2008  | Eskaros et al.    | 604/103.06 |

FOREIGN PATENT DOCUMENTS

| EP | 1642612          | 4/2006  |   |          |
| WO | PCT/US94/04402   | *10/1994| ... | A61M 29/00 |
| WO | PCT/US94/004402  | *10/1994| ... | A61F 2/958 |
| WO | WO 94/23787      | 10/1994 |   |          |
| WO | WO 2008/021019   | 2/2008  |   |          |
| WO | WO 2010/009785   | 1/2010  |   |          |

* cited by examiner

*Primary Examiner* — Jason Flick
*Assistant Examiner* — Leah Stohr
(74) *Attorney, Agent, or Firm* — Workman Nydegger; Jonathan D. Feuchtwang

(57) ABSTRACT

A balloon of a balloon catheter including, in its folded state, a central, inflatable body portion having an outer peripheral wall surface and a plurality of hollow lobes being wrapped around the outer peripheral wall surface and being in fluid communication with the inflatable body portion the lobes including free end portions defining gaps therebetween.

11 Claims, 2 Drawing Sheets

BALLOON OF A BALLOON CATHETER

CROSS-REFERENCE TO RELATED APPLICATIONS

This application is a U.S. Nationalization of PCT Application Number PCT/EP2009/003528 filed May 18, 2009 which claims the benefit of European Patent Application No. 08013291.3 filed Jul. 23, 2008, the entireties of which are incorporated herein by reference.

BACKGROUND

1. Field of the Invention

The present invention relates to an inflatable balloon of a balloon catheter.

2. Relevant Technology

Balloon catheters with expandable balloons are used for expanding devices such as stents at a desired location in a body vessel. The balloon is folded to achieve a low profile and a stent may be crimped onto the folded balloon for introducing the balloon catheter and the stent crimped thereon into the body vessel. The way of designing the inflatable cross section profile of the balloon is essential for the overall performance of the catheter.

Known inflatable balloons of balloon catheters, however, cause an undesirable torque or relative movement on the stent. In their folded state, they often cannot sufficiently hold the crimped-upon stent due to their even surface, and moreover provide an uneven diameter or cross section profile of the balloon as well as an uneven pressure distribution on a balloon expandable stent.

BRIEF SUMMARY

It is, therefore, an object underlying the present invention to provide a balloon that is able to solve the above mentioned problems of the prior art balloons.

The solution of this object may be achieved by at least one of the features of the present invention. The balloon of the balloon catheter according to an embodiment of the present invention includes, in its folded state, a central, inflatable body portion having an outer peripheral wall surface and a plurality of hollow lobes being wrapped around the outer peripheral wall surface of the body portion. These lobes are in fluid communication with the inflatable body portion. The lobes include free end portions defining gaps therebetween.

BRIEF DESCRIPTION OF THE DRAWINGS

Further features and advantages of the present invention will become apparent from the following description of preferred embodiments with reference to the appended drawings, wherein.

DETAILED DESCRIPTION

Figure 1:
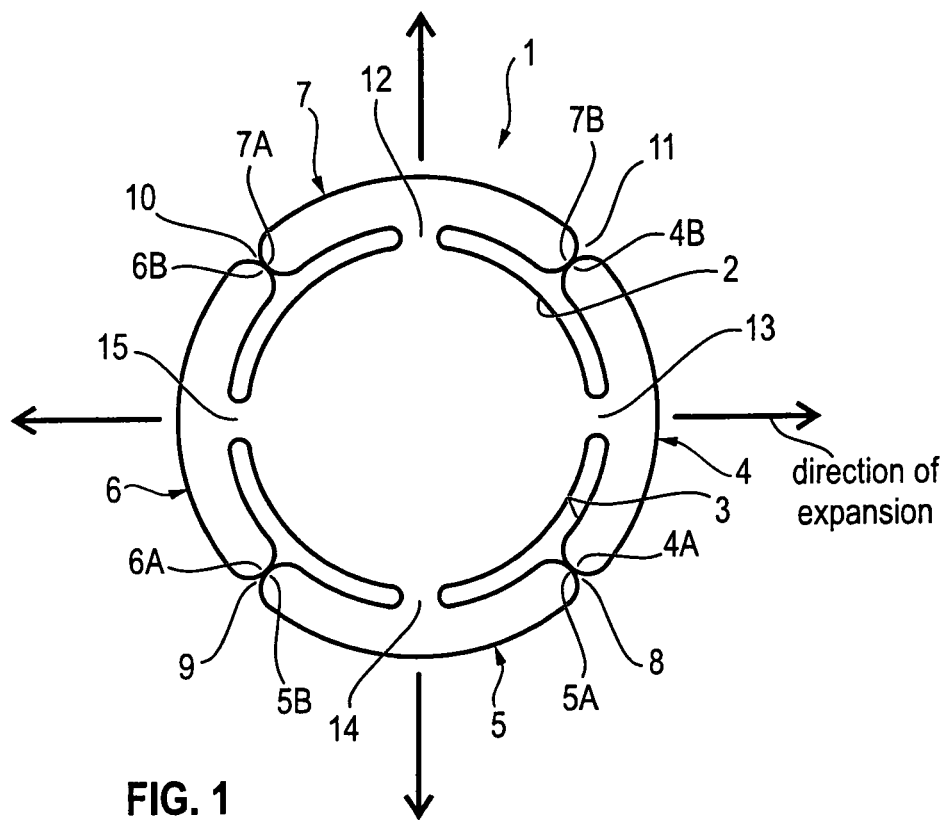
FIG. 1 shows an enlarged cross-sectional view of the balloon according to a first embodiment of the present invention.

FIG. 1 shows an enlarged cross-sectional view of a balloon 1 according to a first embodiment of the present invention. In this illustration, for a better demonstration, a stent around the balloon 1 as well as a guide wire lumen and a guide wire inside the balloon 1 are not depicted. As can be seen from FIG. 1, the balloon 1, shown in its folded state, includes a central inflatable body portion 2 having an outer peripheral wall surface 3 and a plurality of hollow lobes 4, 5, 6, 7, defining mushroom-like configurations, being wrapped around an outer peripheral wall surface 3 of the body portion 2. The lobes 4, 5, 6, 7 include free end portions 4A, 4B, 5A, 5B, 6A, 6B, 7A, 7B. As illustrated, the free end portions 4A, 4B to 7A, 7B, in this embodiment, touch each other. The lobes 4, 5, 6, 7 are in fluid communication with the inflatable body portion 2 through connecting ports 12, 13, 14, 15. The lobes define gaps 8, 9, 10, 11 between the contacting free end portions 4A to 7B. These gaps 8, 9, 10, 11 enable a stent being crimped onto this balloon structure to grip into these gaps 8, 9, 10, 11 for a better fixation.

Figure 2:
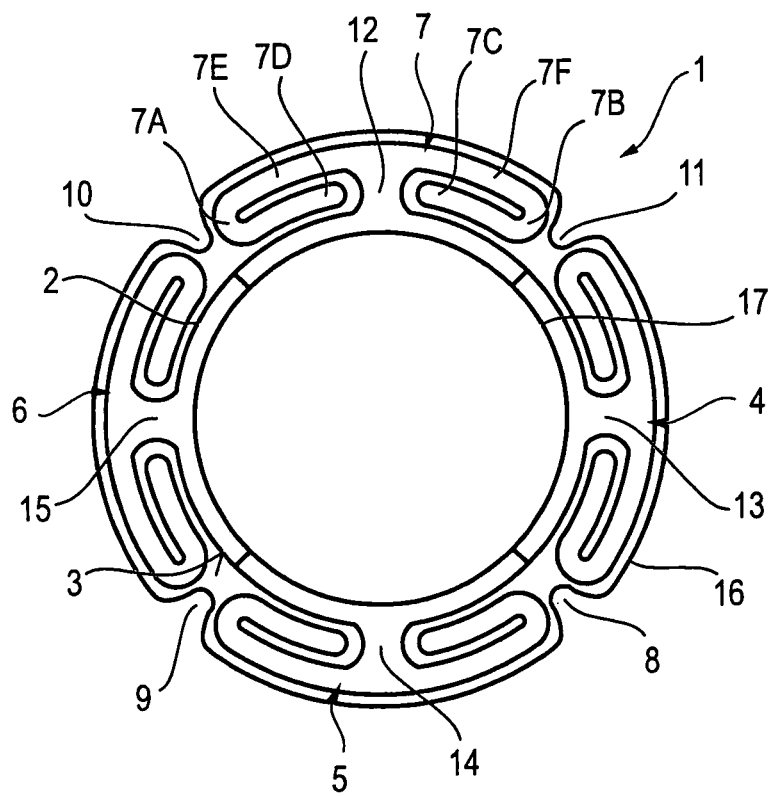
FIG. 2 shows an enlarged cross-sectional view of the balloon including the surrounding stent and a guide wire lumen inside according to a further embodiment of the present invention.

FIG. 2 shows a cross-sectional view of the balloon 1 according to a further embodiment of the present invention. Besides the balloon 1, there are additionally depicted a guide wire lumen 17 inside the body portion 2 represented by a circle line and a stent 16 represented by the solid line surrounding the balloon 1. The configuration of the hollow lobe 4 is exemplarily described for all shown lobes 4, 5, 6, 7 wrapped around the body portion 2. The hollow lobe 4 comprises two wings 7E, 7F extending in opposite directions from the common connecting port 12. Moreover, the wings 7E, 7F include back-fold sections 7C, 7D extending from the free end portions 7A, 7B back to the connecting port 12 and being disposed between the wings 7E, 7F and the wall surface 3. As can be seen from this cross sectional view of FIG. 2, the four shown single segments or lobes 4, 5, 6, 7 do not contact each other, and thus define broader and deeper gaps 8, 9, 10, 11. As a matter of course, an increased number of lobes can be circumferentially disposed around the body portion 2 of the balloon 1 in the same way. The stent 16 crimped on such a folded configuration of the balloon 1 will adapt or embed to a certain degree into these gaps 8, 9, 10, 11 thus causing a locked connection between the stent 16 and the balloon 1 which prevents a rotation as a relative movement between these devices.

Figure 3:
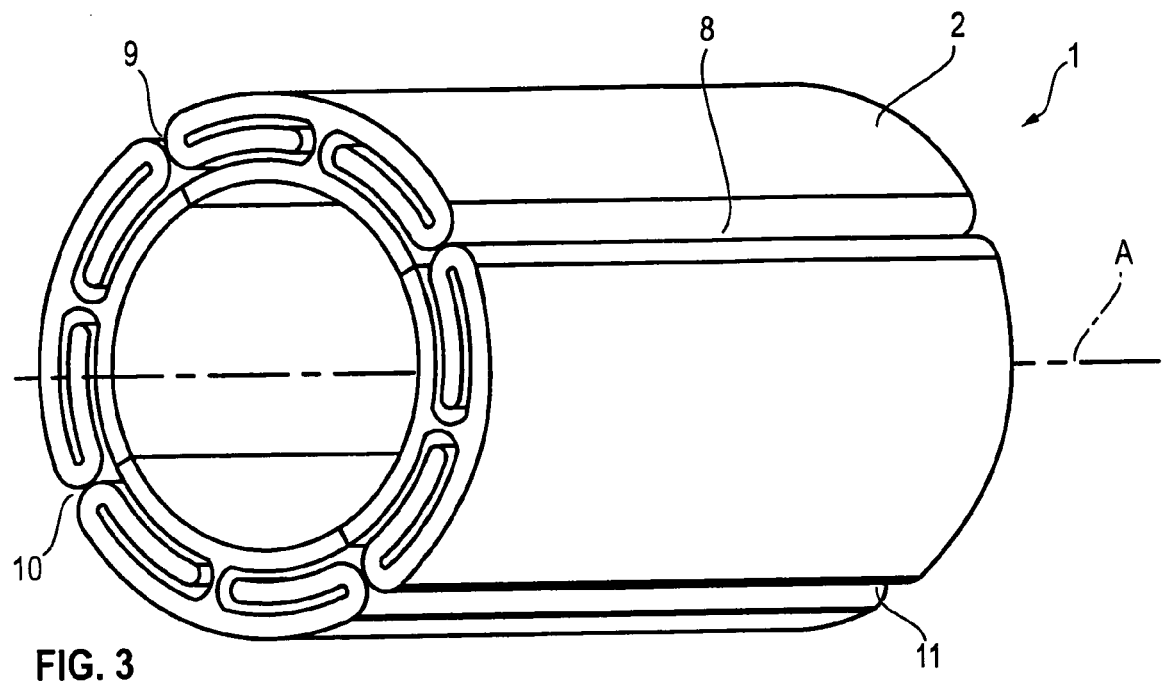
FIG. 3 shows an enlarged perspective view of the balloon of FIG. 2 according to a still further embodiment of the present invention.

FIG. 3 shows an enlarged partial perspective view of the balloon 1 of FIG. 2 according to a still further embodiment of the present invention. As illustrated in FIG. 3, the gaps 8, 9, 10, 11 between the hollow lobes 4, 5, 6, 7, in this case touch each other and extend in parallel to the longitudinal axis A of the body portion 2. Due to this arrangement the stent 16 crimped onto the balloon 1 is fixed by a longitudinal embedment into the gaps 8, 9, 10, 11 and thus preventing the stent from being moved in circumferential direction relative to the balloon 1, as already described in FIG. 2.

Figure 4:
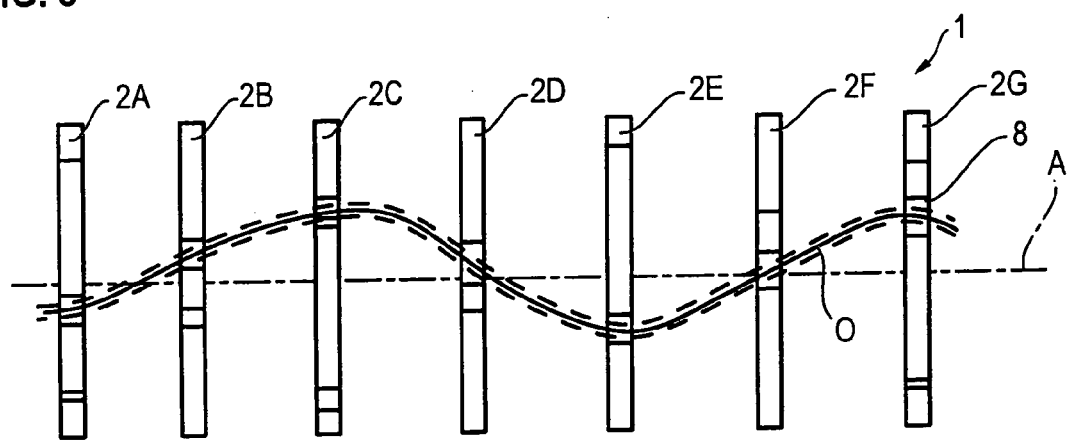
FIG. 4 shows an enlarged side view of cut sections of the balloon of FIG. 2 according to a yet further embodiment of the present invention.

FIG. 4 is an enlarged side view of the balloon 1 from FIG. 2, which is cut in a plurality of sections 2A, 2B, 2C, 2D, 2E, 2F, 2G for a better illustration of a yet further embodiment of the present invention. In this embodiment, the gaps 8 to 11 are disposed according to an offset line O extending in a wave form or sine curve with respect to the longitudinal axis A of the body portion 2. Due to the offset disposition of the gaps 8, according to the offset line O extending along the longitudinal axis A, an improved fixation of the surrounding stent 16 on the balloon 1 in the longitudinal direction as well as in the circumferential direction can be achieved.

Figure 5:
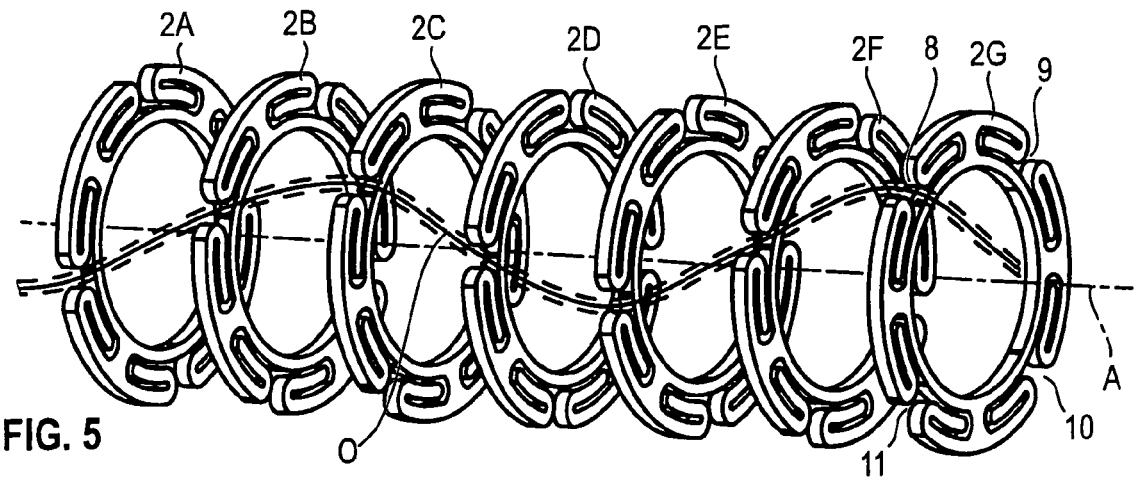
FIG. 5 shows a perspective cross-sectional view of the cut sections of the balloon of FIG. 4.

FIG. 5 shows a perspective cross-sectional view of the cut sections 2A, 2B, 2C, 2D, 2E, 2F, 2G of the body portion 2 of FIG. 4 wherein the course of the offset gaps 8 to 11 according to the offset line O is depicted in more details. The longitudinally changing offset position of the gaps 8 to 11 results in an offset and thus enhanced embedding of the stent 16 into the gaps 8 to 11. In case of a sinusoidal changing offset position of the gaps 8 to 11, the frequency or phase shift thereof may be changed. With alternative wave forms being different from a sine curve changing slopes at any point or cut section of the curve may be selected. Moreover, this offset disposition of the gaps 8 to 11 acts like a locking mechanism to fix the stent 16 on the balloon 1 in both, degrees of freedom, rotation and translation. Due to the structure of the balloon 1, according the present invention, all parts of the surrounding stent 16 that were once slightly embedded or bended into the gaps 8 of the balloon 1 will securely bended back towards the vessel wall when the balloon in use is inflated.

In addition to the written disclosure, reference is herewith made explicitly to the disclosure of the invention in FIGS. 1 to 5.

The invention claimed is:

1. A balloon of a balloon catheter comprising, in its folded state,
   a central, inflatable body portion having an outer peripheral wall surface; and
   a plurality of hollow lobes in fluid communication with the inflatable body portion, the plurality of hollow lobes being formed into folded regions arranged around the outer peripheral wall surface such that adjacent folded regions do not overlap one another, the folded regions including free end portions defining gaps between adjacent folded regions, the folded regions including two wings extending in opposite directions from a common connecting port along the peripheral wall surface, wherein the two wings each include a back-fold section extending from the free end portion back to the common connecting port.

2. The balloon according to claim 1 wherein the free end portions touch each other without overlapping one another.

3. The balloon according to claim 1 wherein the free end portions are spaced from each other.

4. The balloon according to claim 1 wherein the gaps extend in parallel to the longitudinal axis of the body portion.

5. The balloon according to claim 1 wherein each of the gaps is disposed according to an offset line with respect to the longitudinal axis of the body portion.

6. The balloon according to claim 5 wherein a plurality of the lobes is provided.

7. A balloon of a balloon catheter comprising, in its folded state,
   a central, inflatable body portion having an outer peripheral wall surface; and
   a plurality of folded regions arranged around the outer peripheral wall surface, each folded region including two wings that include free end portions extending in opposite directions from a common connecting port that is in fluid communication with the central, inflatable body portion,
   wherein the folded regions include back-fold sections extending from the free end portions back toward the connecting port, the back fold sections being disposed between the wings and the outer peripheral wall surface,
   wherein the plurality of folded regions are arranged such that the free end portions define gaps between adjacent folded regions, and
   wherein the plurality of folded regions are arranged such that the free end portions of adjacent folded regions do not overlap one another.

8. The balloon according to claim 7 wherein the free end portions touch each other without overlapping one another.

9. The balloon according to claim 7 wherein the free end portions are spaced apart from each other.

10. The balloon according to claim 7 wherein the gaps extend in parallel to the longitudinal axis of the body portion.

11. The balloon according to claim 7 wherein each of the gaps is disposed according to an offset line with respect to the longitudinal axis of the body portion.

* * * * *

UNITED STATES PATENT AND TRADEMARK OFFICE
CERTIFICATE OF CORRECTION

PATENT NO.       : 8,702,745 B2                                               Page 1 of 1
APPLICATION NO.  : 13/055341
DATED            : April 22, 2014
INVENTOR(S)      : Nicolas Degen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this

Twenty-ninth Day of September, 2015

Michelle K. Lee
*Director of the United States Patent and Trademark Office*